United States Patent
Imanishi et al.

(10) Patent No.: US 9,415,127 B2
(45) Date of Patent: Aug. 16, 2016

(54) PLASMA TREATMENT METHOD

(71) Applicant: NGK INSULATORS, LTD., Nagoya (JP)

(72) Inventors: Yuichiro Imanishi, Nagoya (JP); Naohiro Shimizu, Miura (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 14/603,659

(22) Filed: Jan. 23, 2015

(65) Prior Publication Data

US 2015/0217013 A1 Aug. 6, 2015

(30) Foreign Application Priority Data

Jan. 31, 2014 (JP) .................................. 2014-017845

(51) Int. Cl.

| | |
|---|---|
| *B01J 19/08* | (2006.01) |
| *A61L 2/00* | (2006.01) |
| *C07C 1/00* | (2006.01) |
| *H05F 3/00* | (2006.01) |
| *A61L 2/14* | (2006.01) |
| *H05H 1/24* | (2006.01) |

(52) U.S. Cl.
CPC ................ *A61L 2/14* (2013.01); *H05H 1/2406* (2013.01); *H05H 2001/2418* (2013.01); *H05H 2001/2437* (2013.01); *H05H 2245/1225* (2013.01)

(58) Field of Classification Search
CPC .............. A61L 2/00; A61L 9/22; A61L 12/00
USPC .............. 422/1, 4, 22, 121, 186.04, 305–306; 204/157.15, 164; 205/147, 637; 250/326; 606/41; 600/6; 604/5
See application file for complete search history.

(56) References Cited

U.S. PATENT DOCUMENTS

| | | | | |
|---|---|---|---|---|
| 5,302,343 A | * | 4/1994 | Jacob ........................ | A61L 2/14 204/164 |
| 2012/0199286 A1 | | 8/2012 | Shionoya et al. | |
| 2012/0306369 A1 | | 12/2012 | Terazawa et al. | |

FOREIGN PATENT DOCUMENTS

| | | |
|---|---|---|
| WO | 2011/065171 A1 | 6/2011 |
| WO | 2012/120928 A1 | 9/2012 |

OTHER PUBLICATIONS

Nobuya Hayashi et al., "*Agricultural Applications of Plasma: Disinfection to Growth Enhancement*," The Institute of Electrical Engineers of Japan Journal, vol. 132, No. 10, 2012, pp. 702-705 (with English translation of pertinent portion).

* cited by examiner

*Primary Examiner* — Monzer R Chorbaji
(74) *Attorney, Agent, or Firm* — Burr & Brown, PLLC (57) ABSTRACT

In a plasma treatment method, at least a surface of a target object is treated using a plasma treatment apparatus at least including a discharge electrode section configured to cause electric discharge based on supply of a high voltage pulse from a pulse power supply, by supplying fluid including nitrogen into the discharge electrode section to generate plasma by electric discharge in the discharge electrode section and applying resultant active species and the fluid to the target object. The flow rate of the fluid is in a range of 20 mm/s to 500 mm/s. Electrical energy per area of the discharge electrode section in the pulse power supply is $1.4 \times 10^4$ ($J/cm^2$) or more. The separation distance from the center of the discharge electrode section to the target object is in a range of 3 mm to 1700 mm.

14 Claims, 12 Drawing Sheets

PLASMA TREATMENT METHOD

CROSS-REFERENCE TO RELATED APPLICATION

This application is based upon and claims the benefit of priority from Japanese Patent Application No 2014-017845 filed on Jan. 31, 2014, the contents of which are incorporated herein by reference.

BACKGROUND OF THE INVENTION

1. Field of the Invention

The present invention relates to a plasma treatment method for performing plasma treatment such as sterilization, etc. by applying active species generated by plasma to a target object (target object of treatment) indirectly.

2. Description of the Related Art

In recent years, attempts to perform sterilization of agricultural crops, foods, etc. using active neutral particles in plasma have been made (see the following reference).

Reference: "Agricultural Applications of Plasma: Disinfection to Growth Enhancement", IEEJ Journal, Vol. 132, No. 10, pp. 702-705, 2012

As apparatuses for generating radicals, in addition an atmospheric pressure barrier electric discharge plasma torch described in the above reference, apparatuses described in International Publications Nos. WO2011/065171 and WO2012/120928 are known.

In the apparatus described in International Publication No. WO2011/065171, an electrode structural body including a first electrode, a second electrode, and a third electrode are provided in a middle of a gas passage. Further, the second electrode is provided on an upstream side of the first electrode, and the third electrode is provided on a downstream side the first electrode. One pole of a pulse power supply is connected to the first electrode, and the other pole of the pulse power supply is connected to the second electrode and the third electrode. Further, the first electrode is provided to cross a first gas passing surface and occupies a part of the first gas passing surface. The second electrode and the third electrode are provided to cross a second gas passing surface and a third gas passing surface and occupy a part of a second gas passing surface and a third gas passing surface, respectively. Accordingly, plasma is generated on the upstream side and the downstream side of the first electrode. Moreover, terminals of the first electrode, the second electrode, and the third electrode do not serve as starting or ending points of electric discharge. Consequently, improvement in the durability of the first electrode, the second electrode, and the third electrode is achieved.

In the apparatus described in International Publication No. WO2012/120928, a passage formation, a transformer, an electrode structural body (anode bar and cathode plate), an anode side feeding path, and a cathode side feeding path are placed in an electrically conductive housing. An extending direction of the anode bar is nonparallel with an extending direction of the cathode plate. The anode bar and the cathode plate cross the passage. The anode bar and the cathode plate are provided apart from each other in an extending direction of the gas passage. The feeding terminal of the anode bar and the positive output terminal of the secondary winding of the pulse power supply are connected electrically, the feeding terminal of the cathode plate and the negative output terminal of the secondary winding are connected electrically. Further, the housing is electrically connected to the cathode side feeding path. In this manner, the waveform of pulse voltage is not disturbed significantly.

SUMMARY OF THE INVENTION

However, in the above reference. International Publications Nos. WO2011/065171 and WO2012/120928, the apparent life of active species generated by plasma, the optimum separation distance to the target object, etc. are not verified, and it is difficult to improve the efficiency of plasma treatment. Therefore, in the conventional technique, in the case of performing plasma treatment, e.g., sterilization by applying active species resulting from plasma generation to a target object indirectly, improvement in the efficiency of plasma treatment is limited.

The present invention has been made taking such a problem into consideration, and an object of the present invention is to provide a plasma treatment method in which in the case of performing plasma treatment such as sterilization, etc. by applying active species resulting from plasma to a target object (target object of treatment), it is possible to improve the efficiency of the plasma treatment.

[1] According to a first aspect of the present invention, a plasma treatment method treats at least a surface of a target object using a plasma treatment apparatus at least including a discharge electrode section having an anode and a cathode and being configured to cause electric discharge between the anode and the cathode based on supply of a high voltage pulse from a pulse power supply, by supplying fluid including nitrogen into the discharge electrode section to generate plasma by the electric discharge in the discharge electrode section and applying resultant active species and the fluid to the target object. A flow rate of the fluid is in a range of 20 mm/s to 500 mm/s. Electrical energy per area of the discharge electrode section in the pulse power supply is $1.4 \times 10^4$ J/cm$^2$ or more. A separation distance from a center of the discharge electrode section to the target object is in a range of 3 mm to 1700 mm.

In the structure, in the case of performing plasma treatment such as sterilization, etc. by applying active species produced by plasma to a target object (target object of treatment), improvement in the efficiency of the plasma treatment is achieved.

[2] In the present invention, preferably, the separation distance is in a range of 30 mm to 500 mm.

[3] In the present invention, preferably, a pulse frequency of the high voltage pulse outputted from the pulse power supply is in a range of $1 \times 10^3$ pulses/sec to $3 \times 10^4$ pulses/sec.

[4] In the present invention, preferably, the pulse frequency of the high voltage pulse outputted from the pulse power supply is in a range of $3 \times 10^3$ pulses/sec to $1 \times 10^4$ pulses/sec.

[5] In the present invention, the discharge electrode section may include one or more first discharge electrodes as the anode and one or more second discharge electrodes as the cathode, and the first discharge electrode and the second discharge electrode may be arranged and separated from each other in a flow direction of the fluid. In the structure, the fluid flows in a direction to maximize the electric field generated between the first discharge electrode and the second discharge electrode. Therefore, improvement in the efficiency of generating the active species is achieved. Instead of the two-stage structure of the first discharge electrode and the second discharge electrode, three-stage structure of the first discharge electrode, the second discharge electrode, and the first discharge electrode, or the second discharge electrode, the first discharge electrode, and the second discharge electrode may be adopted. It is a matter of course that structure of four or more stages may be adopted. By adopting multi-stage structure, it is possible to increase the amount of generated active species (e.g., $N_2$ radicals).

[6] Preferably, the first discharge electrode includes one or more first electrode sections having a first conductor, the second discharge electrode includes one or more second electrode sections having a second conductor, and the first electrode section and the second electrode section are separated from each other, and as viewed from the flow direction of the fluid to the discharge electrode section, the first electrode section and the second electrode section have a crossing positional relationship. By increasing the separation distance between the first electrode section and the second electrode section, the voltage applied between the first electrode section and the second electrode section becomes large, and intensity of the active species, e.g., $N_2$ radical is improved.

[7] In this case, as viewed from the flow direction of the fluid to the discharge electrode section, the first electrode section and the second electrode section may form a plurality of grids. By adopting the grid structure, it is possible to alleviate the electric field generated between the first electrode section and the second electrode section, and generate wide plasma. Consequently, improvement in the efficiency of generating active species is achieved.

[8] Further, as viewed from the flow direction of the fluid to the discharge electrode section, number of crossing portions between the first electrode section and the second electrode section may be in a range of 1 to 25 portions per square centimeters (one portion/$cm^2$ to 25 portions/$cm^2$).

[9] In this case, the arrangement pitch of the crossing portions may be in a range of 2 to 15 mm.

[10] Preferably, the arrangement pitch of the crossing portions is in a range of 4 to 6.5 mm.

[11] Preferably, a ratio of a distance between high potential electrodes to a distance between facing electrodes is in a range of 0.5 to 3. The distance between high potential electrodes is the distance between the centers of the adjacent first electrode sections, i.e., the arrangement pitch of the first electrode sections. The distance between facing electrodes represents the distance between the crossing part of the first electrode section and the crossing part of the second electrode section.

[12] In this case, more preferably, a ratio of a distance between high potential electrodes to a distance between facing electrodes is in a range of 0.8 to 1.3.

[13] Further, the first electrode section may include the first conductor and a first ceramic layer covering the first conductor, and the second electrode section may include the second conductor and a second ceramic layer covering the second conductor.

[14] In the present invention, the pulse power supply may include a pulse generator configured to apply the high voltage pulse between the anode and the cathode and a pulse controller configured to control the pulse generator to generate electric discharge between the anode and the cathode. The pulse generator may include a pulse generator circuit having a transformer and a switch connected in series at both ends of a direct current power supply unit, configured to accumulate inductive energy in the transformer when ON control of the switch is implemented by the pulse controller, and to generate the high voltage pulse on a secondary side of the transformer when OFF control of the switch is implemented by the pulse controller.

In the plasma treatment method according to the present invention, in the case of performing plasma treatment such as sterilization, etc. by applying active species generated in plasma indirectly to the target object (target object of treatment), improvement in the plasma treatment is achieved.

The above and other objects, features, and advantages of the present invention will become ore apparent from the following description when taken in conjunction with the accompanying drawings in which a preferred embodiment of the present invention is shown by way of illustrative example.

DETAILED DESCRIPTION OF THE INVENTION

Hereinafter, an example of an embodiment of a plasma treatment method according to the present invention will be described with reference to FIGS. 1 to 12. It should be noted that, in this description, a numeric range of "A to B" includes both the numeric values A and B as lower and upper limit values.

Figure 1:
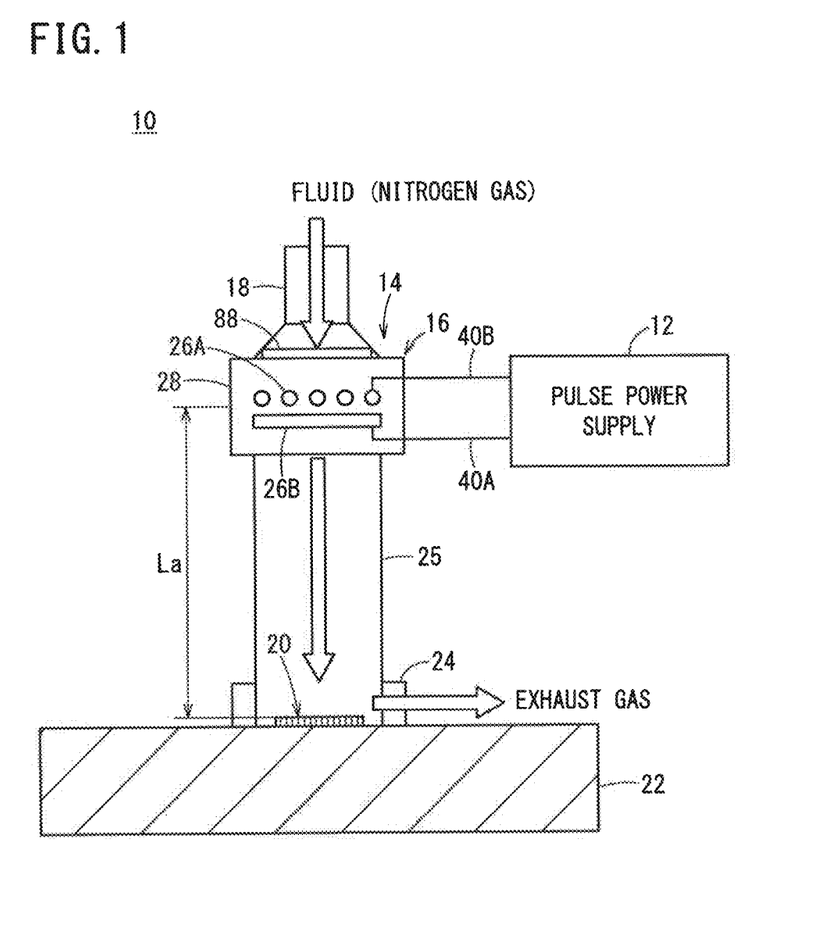
FIG. 1 is a diagram showing structure of a plasma treatment apparatus used in a plasma treatment method according to an embodiment of the present invention.

The plasma treatment method according to the embodiment of the present invention is performed, e.g., using a plasma treatment apparatus 10 shown in FIG. 1.

This plasma treatment apparatus 10 includes a pulse power supply 12 for generating high voltage pulse and a reactor 14 for generating plasma by application of the high voltage pulse from the pulse power supply 12 to the reactor 14.

The reactor 14 includes a discharge electrode section 16 having an anode and a cathode for causing electric discharge between the anode and the cathode based on the supply of high voltage pulse from the pulse power supply 12 and a fluid guide section 18 for guiding fluid including nitrogen to the discharge electrode section 16.

Further, this plasma treatment apparatus 10 supplies fluid into the discharge electrode section 16 to generates plasma by the electric discharge in the discharge electrode section 16. Further, the plasma treatment apparatus 10 applies the resulting active species and the fluid to a target object 20 of the plasma treatment, to treat at least a surface of the target object 20. Therefore, by applying this plasma treatment apparatus 10, e.g., to sterilization treatment for allowing the plasma treatment apparatus 10 to serve as a sterilization apparatus, sterilization of the target object 20 can be performed. Preferably, for example, the target object 20 is placed on a base frame 22 having a heater (not shown), and kept within a predetermined temperature range. It is a matter of course that a heater may be provided inside of the fluid guide section 18 to maintain the temperature of the fluid. By increasing the temperature of the fluid, the required treatment time (time required for sterilization treatment, surface treatment, etc.) can be shortened, and improvement in the efficiency of the treatment is achieved. It should be noted that, preferably, the temperature of the fluid is in a range of 50° C. to 60° C., e.g., in the case of sterilization treatment, and in a range of 70° C. to 80° C. in the case of metal surface treatment, etc.

Figure 2:
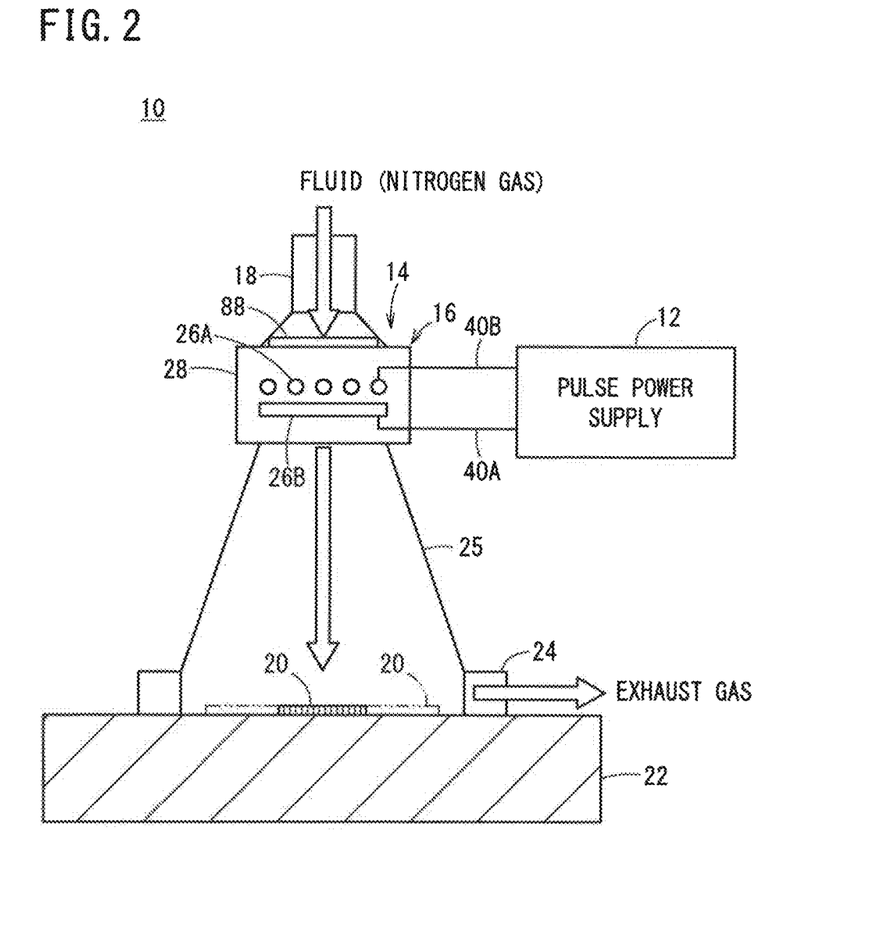
FIG. 2 is a diagram showing another example of the plasma treatment apparatus.

Further, preferably, the space between the discharge electrode section 16 and the target object 20 should be covered by a cylindrical tube 25 (e.g., acrylic tube) having an exhaust section 24 at its lower position for preventing oxygen from being mixed with fluid (fluid containing active species) passing through the discharge electrode section 16. The tube 25 may have a cylindrical shape having a constant diameter as shown in FIG. 1, or may have a skirt shape having a diameter increased toward the flow direction of the fluid as shown in FIG. 2. In the example of FIG. 2, the plane size of the target object 20 may be smaller than the plane size of the discharge electrode section 16, or may be larger than the plane size of the discharge electrode section 16.

The "active species" herein refers to, for example, radicals (neutral non-light emitting species which do not obey the octet rule), excited species where the internal energy state of molecules/atoms is changed due to collision of high speed electrons (excited state), ions, light emitting species, and molecules (e.g., ozone) produced by reaction of the active species and fluid molecules.

Figure 3:
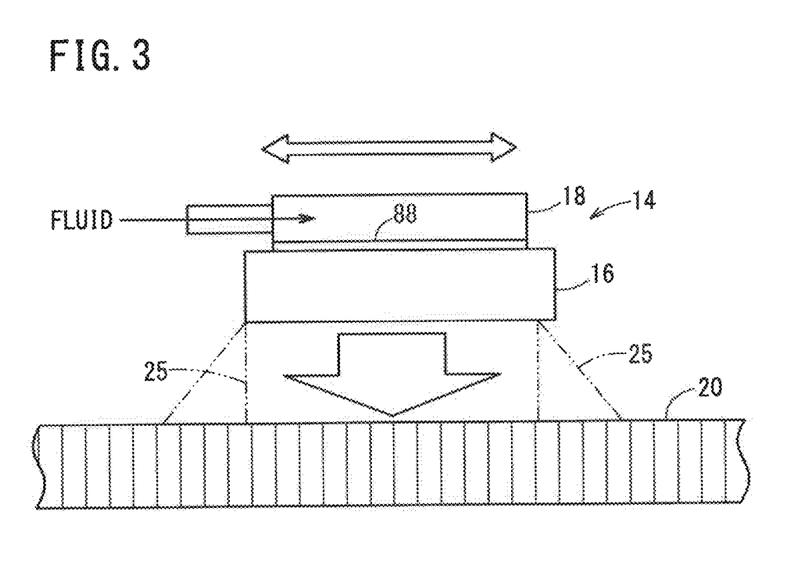
FIG. 3 is a diagram showing another example of using the plasma treatment method according to the embodiment of the present invention.

In the example of FIG. 1, the plane size of the target object 20 is smaller than the plane size of the discharge electrode section 16. Alternatively, the plane size of the target object 20 may be equal to or larger than the plane size of the discharge electrode section 16. In the case of applying plasma treatment to the target object 20 having the plane size which is larger than the plane size of the discharge electrode section 16, as shown in FIG. 3, the plasma treatment may be applied to the front surface (and the back surface) of the target object 20 while moving (scanning) the fluid guide section 18 and the discharge electrode section 16 along the target object 20. In this case, preferably, at the time of movement, the tube 25 as shown in FIGS. 1 and 2 is attached.

Figure 4:
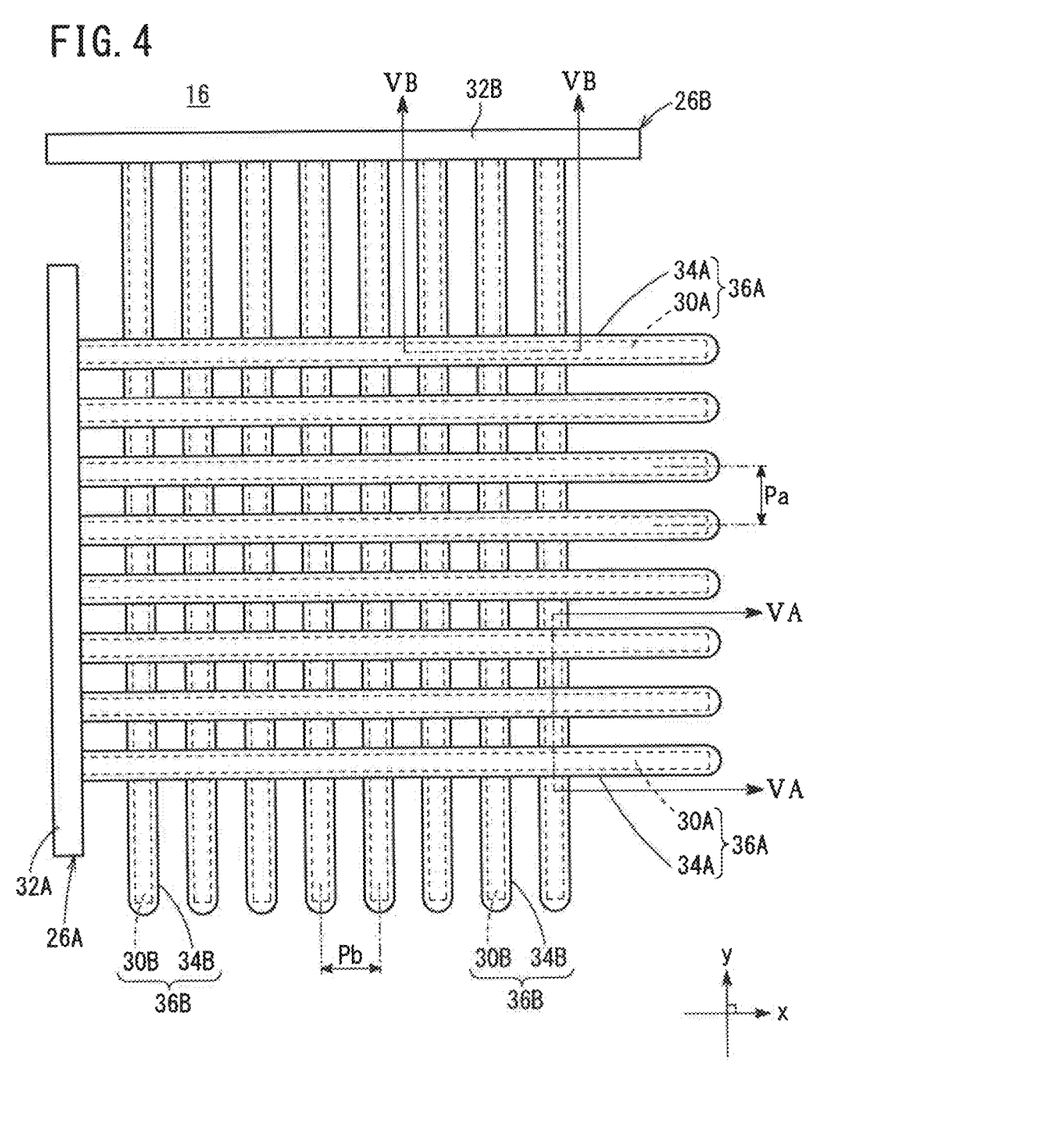
FIG. 4 is a front view showing an example of structure of a first discharge electrode and a second discharge electrode in a discharge electrode section.

As shown in FIG. 4, the discharge electrode section 16 includes a first discharge electrode 26A as an anode, a second discharge electrode 26B as a cathode, and a case 28 (see FIG. 1) holding the first discharge electrode 26A and the second discharge electrode 26B to have a predetermined positional relationship. The first discharge electrode 26A and the second discharge electrode 26B are arranged in the flow direction. The first discharge electrode 26A and the second discharge electrode 26B are spaced from each other. In the structure, the fluid flows in a direction to maximize the electric field generated between the first discharge electrode 26A and the second discharge electrode 26B. Therefore, improvement in the efficiency of generating the active species is achieved. Instead of the two-stage structure of the first discharge electrode 26A and the second discharge electrode 26B, three-stage structure of the first discharge electrode 26A, the second discharge electrode 26B, and the first discharge electrode 26A, or the second discharge electrode 26B, the first discharge electrode 26A, and the second discharge electrode 26B may be adopted. It is a matter of course that structure of four or more stages may be adopted. By adopting multi-stage structure, it is possible to increase the amount of generated active species (in this case, $N_2$ radicals).

As shown in FIG. 4, the first discharge electrode 26A includes a plurality of bar shaped first conductors 30A extending in a first direction (x direction) and arranged in a second direction (y direction) perpendicular to the first direction, a first common conductor 32A connecting the plurality of first conductors 30A, and first ceramic layers 34A covering at least the first conductors 30A. An area including the first conductor 30A and the first ceramic layer 34A covering the first conductor 30A is referred to as a first electrode section 36A.

The second discharge electrode 26B includes a plurality of bar shaped second conductors 30B extending in the second direction (y direction) and arranged in the first direction (x direction), a second common conductor 32B connecting the plurality of second conductors 30B, and second ceramic layers 34B covering at least the second conductors 30B. An area including the second conductor 30B and the second ceramic layer 34B covering the second conductor 30B is referred to as a second electrode section 36B.

Copper, iron, tungsten, stainless steel, platinum, etc. may be used for the first conductors 30A and the second conductors 30B. Alumina, silica, titania, zirconia, etc. may be used for the first ceramic layers 34A and the second ceramic layers 34B.

Figure 5A:
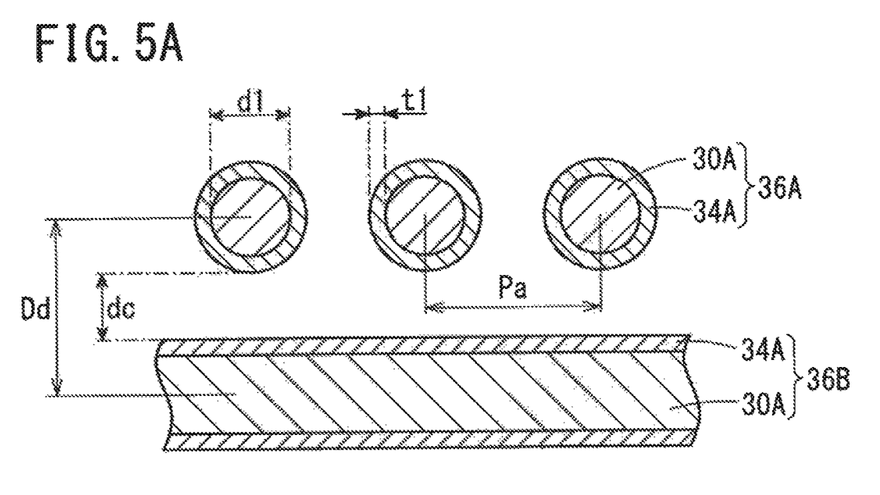
FIG. 5A is a cross sectional view taken along a line VA-VA in FIG. 4.
Figure 5B:
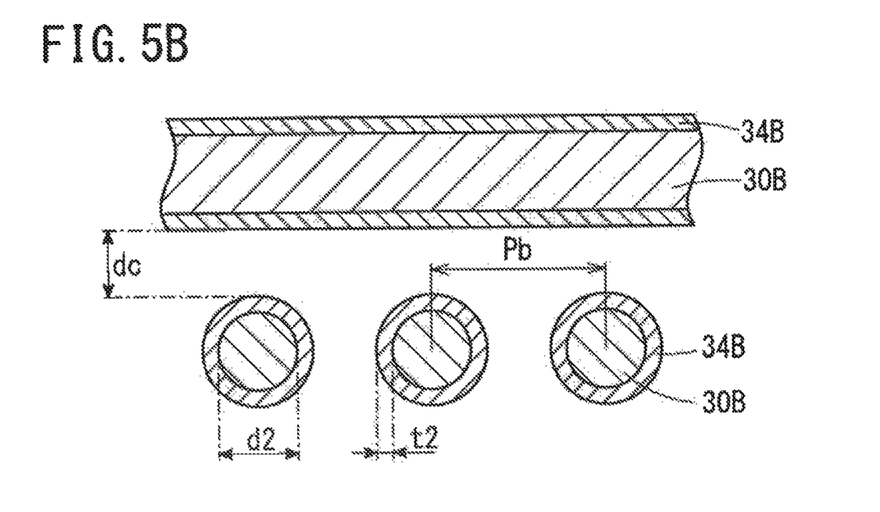
FIG. 5B is a cross sectional view taken along a line VB-VB in FIG. 4.

As shown in FIGS. 5A and 5B, the diameters d1 and d2 of the first conductors 30A and the second conductors 30B are in a range of 200 to 1000 μm. Further, no pores having the size of 50 μm or more are formed in either of the first ceramic layers 34A covering the first conductors 30A or the second ceramic layers 34B covering the second conductor 30B. If the first ceramic layers 34A and the second ceramic layers 34B have a large porosity expressed in the order of percentage, dielectric breakdown may occur easily due to the voltage applied to ceramics. In the presence of only one closed pore having the size of 50 μm as a whole, dielectric breakdown may occur from the portion of the closed pore to cause arc plasma, and to cause dissolution of ceramics. Ideally, no closed pore should be present. It is desirable that diameters of all of the closed pores dispersed in the material are less than 10 μm.

The dimensions are determined to conform to the following inequality expressions:

$$0.1 < Aa1/Ab1 < 1.0$$

$$0.08 < Aa2/Ab2 < 2.0$$

where Aa1 denotes the surface area of the first conductor 30A and Ab1 denotes the surface area of the first ceramic layer 34A, in the cross section of the first electrode section 36A taken in a direction perpendicular to the axial direction, and Aa2 denotes the surface area of the second conductor 30B and Ab2 denotes the surface area of the second ceramic layer 34B, in the cross section of the second electrode section 36B taken in a direction perpendicular to the axial direction.

If the first ceramic layer 34A and the second ceramic layer 34B are thick, the electric field intensity is lowered, and the amount of energy given to electrons is decreased. Consequently, generation of radicals is reduced. That is, since dielectric substance between the first conductor 30A and the second conductor 30B is increased, apparent capacitance component is increased, and it becomes difficult to achieve the steep voltage rise rate (dV/dt). Therefore, it is desired that the above ranges are satisfied.

The diameters d1 and d2 of the first conductor 30A and the second conductor 30B affect the electric field intensity. In particular, high voltage is applied to the anode (first conductor 30A), and the smaller the diameter d1 of the anode becomes, the higher the electric field intensity of the surface of the anode becomes. Therefore, it is preferable to adopt narrow conductors for the first conductor 30A and the second conductor 30B. However, the strength of the narrow conductors is limited, and it is not possible to maintain the shape of the narrow conductors satisfactorily. For this reason, it is preferable that the diameter d1 of the first conductor 30A is in a range of 0.2 to 0.5 mm, and the thickness t1 of the first ceramic layer 34A is in a range of 0.25 to 0.65 mm. Further, it is preferable that the diameter d2 of the second conductor 30B is in a range of 0.5 to 1.0 mm, and the thickness t2 of the second ceramic layer 34B is in a range of 0.25 to 1.25 mm.

The case 28 has, e.g., a circular through hole at its center for allowing fluid to flow through the through hole. A connector portion (not shown) connecting the first common conductor 32A (see FIG. 4) and a positive pole side cable 40A (see FIG. 1) from the pulse power supply 12, and a connector portion (not shown) connecting the second common conductor 32B (see FIG. 4) and a negative pole side cable 40B (see FIG. 1) from the pulse power supply 12 are placed in an outer area of the case 28.

Further, at the time of attaching the first discharge electrode 26A and the second discharge electrode 26B inside the case 28, a plurality of the first electrode sections 36A and a plurality of the second electrode sections 36B face one another. As viewed from the flow direction of the fluid to the discharge electrode section 16, the first electrode section 36A and the second electrode section 36B (see FIG. 4) are held to have a crossing positional relationship (positional relationship of skew lines). That is, the first conductor 30A and the second conductor 30B are held to have a crossing positional relationship (positional relationship of skew lines). In this state, the crossing portion where the first electrode section 36A and the second electrode section 36B are crossing with each other is exposed through the through hole of the case 28. By increasing the separation distance between the first electrode section 36A and the second electrode section 36B, the voltage applied between the first electrode section 36A and the second electrode section 36B is increased, and it is possible to improve the $N_2$ radical intensity.

As shown in FIG. 4, as viewed from the flow direction of the fluid to the discharge electrode section 16, a plurality of grids are formed by the first electrode sections 36A (first conductors 30A) and the second electrode sections 36B (second conductors 30B). By adopting the grid structure, it is possible to alleviate or relax the electric field generated between the first electrode section 36A and the second electrode section 36B, and generate wide plasma. Consequently, improvement in the efficiency of generating $N_2$ radicals is achieved. In this case, it is possible to select the number of crossing portions between the first electrode section 36A (first conductor 30A) and the second electrode section 36B (second conductor 30B) in a range of 1 to 25 portions per square centimeters (one portion/cm$^2$ to 25 portions/cm$^2$). Further, it is possible to select the arrangement pitch of the crossing portions in a range of to 2 to 15 mm, preferably, 3 to 15 mm, and more preferably 4 to 6.5 mm. The crossing portion herein means a portion where the first electrode section 36A and the second electrode section 36B are crossing with each other. Further, as described later, the crossing part of the first electrode section 36A means a portion corresponding to the crossing portion, in the first electrode section 36A. Likewise, the crossing part of the second electrode section 36B means a portion corresponding to the crossing portion, in the second electrode section 36B.

The arrangement pitch Pb of the second electrode sections 36B as a cathode may be small, e.g., in a range of about 1 to 10 mm. It is preferable that the arrangement pitch Pa of the first electrode sections 36A as the anode is configured to be positively correlated with the gap dc from the second electrode section 36B (see FIGS. 5A and 5B).

Figure 6:
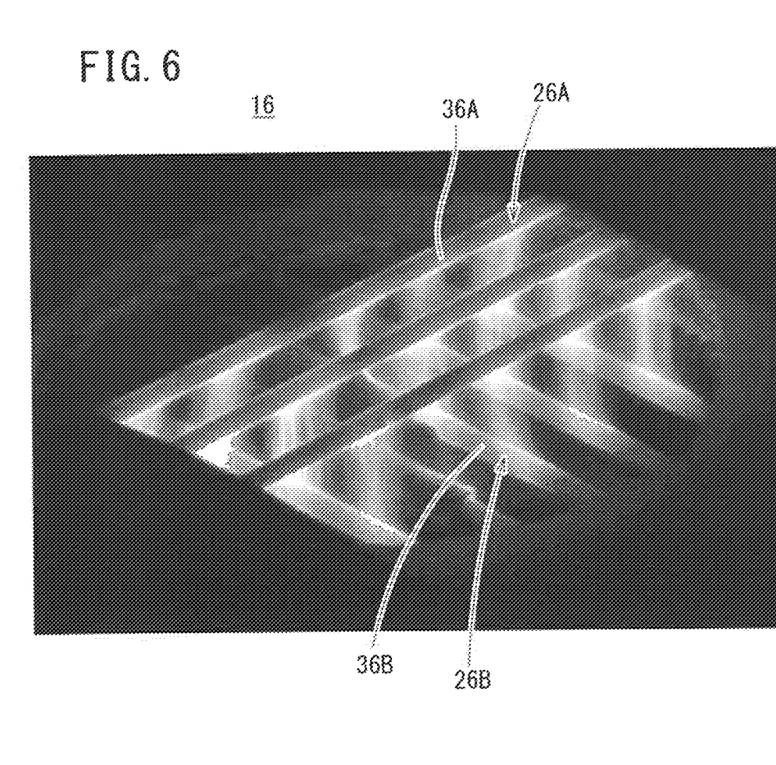
FIG. 6 is a perspective view showing a state where plasma is generated between the first discharge electrode and the second discharge electrode.

Then, the positive pole of the pulse power supply 12 is connected to the first discharge electrode 26A (anode), and the negative pole of the pulse power supply 12 is connected to the second discharge electrode 26B (cathode). Thus, an electric field oriented from the first discharge electrode 26A to the second discharge electrode 26B is applied to the gap between the first electrode section 36A and the second electrode section 36B. Consequently, an ion sheath layer (state where a large number of ions are aggregated) is formed adjacent to a surface of the second electrode section 36B facing the first electrode section 36A, and plasma is generated in the gap between the first electrode section 36A and the second electrode section 36B. FIG. 6 shows a state where plasma is generated between the first electrode section 36A of the first discharge electrode 26A and the second electrode section 36B of the second discharge electrode 26B.

Next, a preferred range of layout in the case where the first electrode section 36A is a high potential electrode, and the second electrode section 36B is a ground electrode will be explained. This explanation is applicable to the case where the second electrode section 28B is a high potential electrode and the first electrode section 28A is a ground electrode.

Firstly, assuming that the second electrode section 36B extends in the x direction and the crossing part of the second electrode section 36B crossing with the first electrode section 36A is the origin O, the electric field intensity E(x) in the x direction between one first electrode section 36A and one second electrode section 36B is obtained by the following equation:

$$E(x)=V/k(x)$$

where k(x) denotes the distance between a point spacing by a distance x in the x direction from the crossing part of the first electrode section 36A crossing with the second electrode section 36B and the second electrode section 36B (origin O), and V denotes the applied voltage.

It should be noted that the distance k(x) can be determined from $k(x)=\sqrt{(Dd^2+x^2)}$
where Dd (see FIG. 5A) denotes the distance between the crossing part of the first electrode section 36A and the crossing part of the second electrode section 36B.

Therefore, the electric field intensity E(x) is the highest at the origin O. As the value of x gets larger, the electrical field intensity E(x) gets smaller. That is, it is considered that 1/k(x) denotes a coefficient indicating contribution to the electrical field intensity in the x direction.

Thus, an electric field (strictly speaking, integrated electric field) produced by summing electric field intensities in the x direction including the low electric field intensity at each of both sides to the high electric field intensity at the center (origin) is concentrated at the crossing part of the first electrode section 36A crossing with the second electrode section 36B, and plasma is formed (generated).

For the reasons stated above, as the x gets larger, the electrical field intensity gets smaller. However, concentration of the electrical field at the first electrode section 36A is increased. That is, as the arrangement pitch Pa of the first electrode sections 36A becomes large, the summed electrical field applied to the crossing part is increased, electrical discharge tends to occur easily, and plasma is stabilized. Therefore, since concentration of the electrical field occurs most effectively when there is only one first electrode section 36A without any other first electrode sections 36A having the same potential, electric discharge is stabilized. Further, since contribution to the electric field intensity from where x is large is small, another first electrode section 36A should be placed at a distance having small contribution to widen the total plasma area, and increase the amount of generated active species.

However, if the number of first electrode sections 36A is excessively large, the following problems may occur. That is, as for the crossing part of the outermost first electrode section 36A, since the first electrode section 36A is not present on one side, the electric field intensity is applied from the surrounding area additionally. In this case, if the number of first electrode sections 36A is increased, since the arrangement pitch Pa of the first electrode sections 36A becomes small, and the electric field intensity applied to the outermost first electrode section 36A becomes higher than the electric field intensity applied to the other first electrode sections 36A. Therefore, plasma is formed only in the surrounding area inefficiently.

Next, $n \times \Sigma(1/k)$ relative to Pa/Dd will be described with reference to a graph of FIG. 7.

$\Sigma(1/k)$ is the sum of $(1/k)$ obtained by dividing the electric field intensity by the applied voltage. The number n is a number of crossing portions between the first electrode sections 36A and the second electrode sections 36B. If the arrangement pitch Pa of the first electrode sections 36A is increased, though the electric field intensity applied to the first electrode section 36A becomes high, the number n of crossing portions is decreased. Therefore, $n \times \Sigma(1/k)$ denotes a value obtained by multiplying a value in proportion to an accumulated value of the electric field intensity applied from the second electrode section 36B to the crossing part of the first electrode section 36A crossing with the second electrode section 36B by the number n of the crossing portions, i.e., the sum value of the accumulated electric field intensity of the plasma generating positions (crossing portions) in the CPG plane. This sum value is a value positively correlated with the amount of generated active species.

Figure 7:
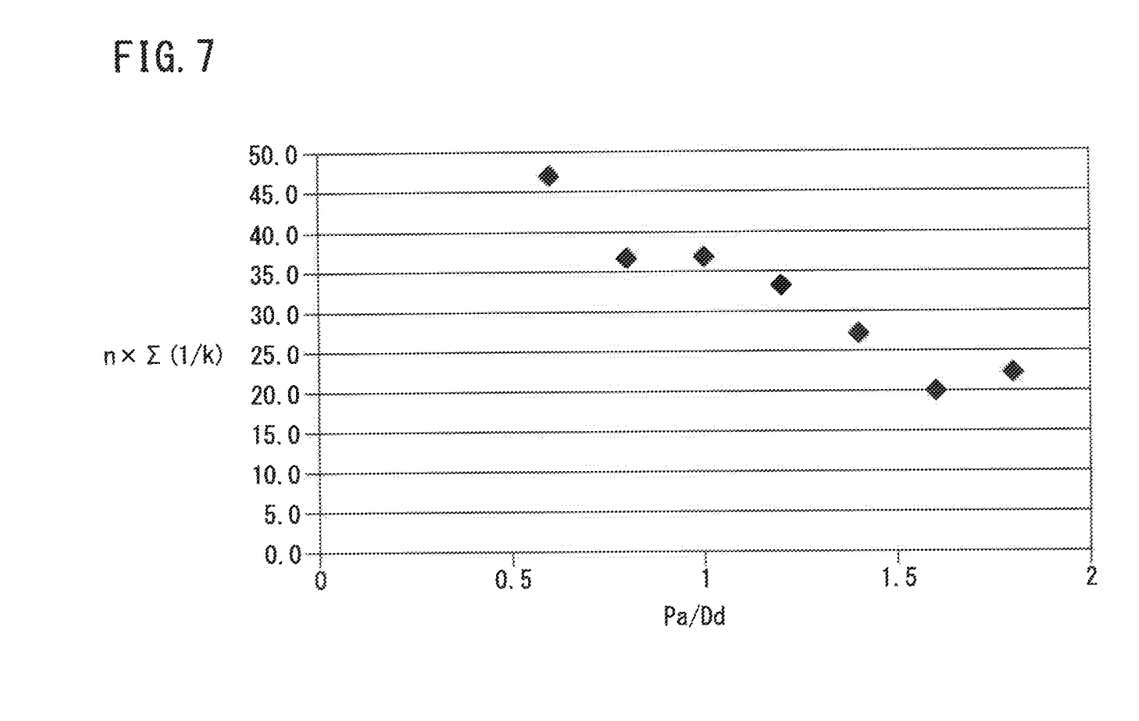
FIG. 7 is a graph showing a change of n×Σ(1/k) (sum of (1/k) obtained by dividing the electric field intensity by the applied voltage) relative to the ratio (Pa/Dd) of the distance between high potential electrodes to the distance between facing electrodes.

As shown in FIG. 7, in the relationship between $n \times \Sigma(1/k)$ and Pa/Dd, if Pa/Dd is small, $n \times \Sigma(1/k)$ is large, and ideally preferable. If the distance Dd is constant, and the arrangement pitch Pa is small, as described above, the electric field intensity applied to the outermost first electrode section 36A is larger than the electric field intensity applied to other first electrode sections 36A, and plasma is formed only in the surrounding area inefficiently. That is, electric discharge becomes unstable, and non-uniform. The same thing can be said in the case where the arrangement pitch Pa is constant and the distance Dd is large. Conversely, if the distance Dd is constant and the arrangement pitch Pa is large, since the electric field intensity concentrated at the crossing portion is increased, electric discharge occurs to a greater extent. However, since the number of the crossing portions is reduced, the streamer is reduced undesirably. The same thing can be said in the case where the arrangement pitch Pa is constant and the distance Dd is small.

That is, it is not possible to simply conclude that $n \times \Sigma(1/k)$ having a large value is suitable. It can be understood that there is a preferable range for causing streamer electric discharge which generates active species. Specifically, the ratio of the arrangement pitch Pa (distance between high potential electrodes) of the first electrode sections 36A (high potential electrodes) to the distance Dd between facing electrodes (Pa/Dd) is preferably, in a range of 0.5 to 3, and more preferably, in a range of 0.8 to 1.3.

Next, structure of the pulse power supply 12 will be described with reference to FIG. 8.

Figure 8:
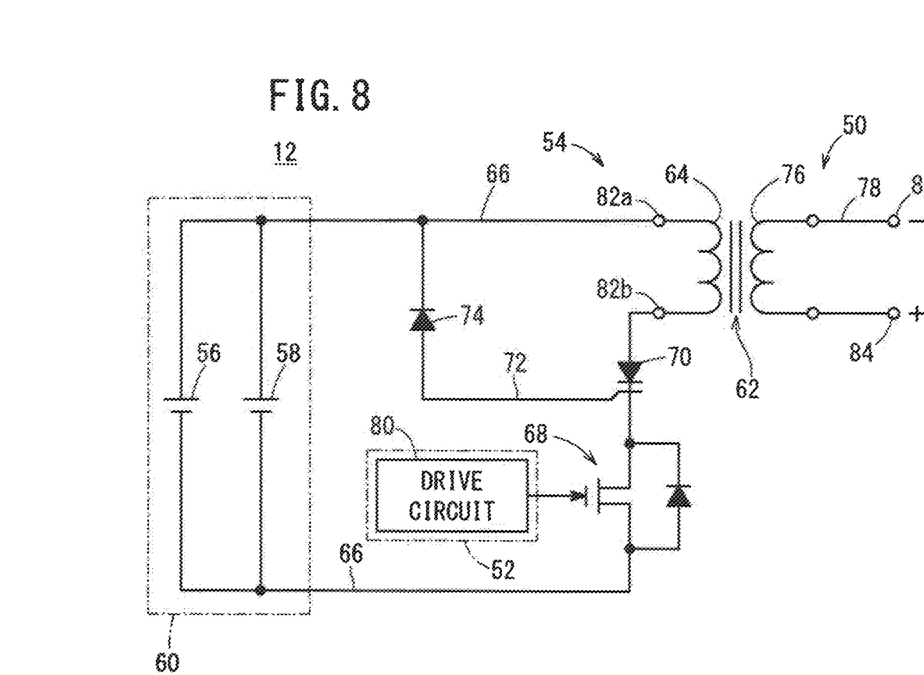
FIG. 8 is a circuit diagram showing structure of a pulse power supply.

As shown in FIG. 8, the pulse power supply 12 has a pulse generator 50 for applying high voltage pulse between the anode and the cathode, and a pulse controller 52 for controlling the pulse generator 50 to cause electric discharge between the anode and the cathode.

The pulse generator 50 includes a pulse generator circuit 54 having the following structure, for example. Specifically, this pulse generator circuit 54 includes: a direct current power supply unit 60 having a direct current power supply 56 for supplying direct current and a capacitor 58 for stabilizing supply of the direct current from the direct current power supply 56; a transformer 62 for accumulating inductive energy; a direct current supply channel 66 to a primary winding 64 of the transformer 62; a MOSFET (metal oxide semiconductor field effect transistor) 68 and an SI-thyristor 70 for opening/closing the supply channel 66; a biasing channel 72 to a gate of the SI-thyristor 70; a diode 74 for suppressing flow of electrical current into the gate of the SI-thyristor 70 and permitting flow of electrical current from the gate of the SI-thyristor 70; and an output channel 78 of the pulse voltage from a secondary winding 76 of the transformer 62. The pulse controller 52 has a drive circuit 80 for driving the MOSFET 68.

The SI-thyristor 70 and the MOSFET 68 are inserted into the supply channel 66 in series such that when the SI-thyristor 70 and the MOSFET 68 are turned on, the supply channel 66 is closed, and when the SI-thyristor 70 and the MOSFET 68 are turned off, the supply channel 66 is opened. One end 82a of the primary winding 64 is connected to the positive pole of the direct current power supply 56 and one end of the capacitor 58, the anode of the SI-thyristor 70 is connected to the other end 82b of the primary winding 64, the cathode of the SI-thyristor 70 is connected to the drain of the MOSFET 68, and the source of the MOSFET 68 is connected to the negative pole of the direct current power supply 56 and the other end of the capacitor 58. The gate of the SI-thyristor 70 is connected to one end 82a of the primary winding 64 through the diode 74 by the biasing channel 72. The cathode of the diode 74 is connected to one end 82a of the primary winding 64, and the anode of the diode 74 is connected to the gate of the SI-thyristor 70. Using the diode 74, the SI-thyristor 70 is positively biased by voltage driving, and negatively biased by current driving. Instead of the transformer 62, an inductor having a single winding may be used to directly output the pulse voltage from the inductor.

Then, when input of an ON signal from the drive circuit 80 to the MOSFET 68 is started, and the MOSFET 68 is turned on, the gate of the SI-thyristor 70 is positively biased, and the SI-thyristor 70 is turned on. Thus, the supply channel 66 is closed. When the supply channel 66 is closed, supply of direct current to the primary winding 64 is started, and accumulation of the inductive energy in the transformer 62 is started.

When input of the ON signal from the drive circuit 80 to the MOSFET 68 is finished and the MOSFET 68 is turned off, by the inductive electromotive force produced in the primary winding 64, the gate of the SI-thyristor 70 is negatively biased, and the SI-thyristor 70 is turned off rapidly. Thus, the supply channel 66 is opened rapidly. When the supply channel 66 is opened rapidly, the inductive electromotive force is produced in the secondary winding 76 by mutual induction, and pulse voltage having significantly large rate of rise dV/dt of the voltage V relative to time at leading edge is outputted between a positive pole 84 and a negative pole 86 from the secondary winding 76.

It is desirable that the pulse width of the pulse voltage is in a range of 10 to 1000 ns full width at half maximum (FWHM). It is desirable that the rate of rise dV/dt relative to time at the leading edge of the voltage V is 30 to 3000 kV/μs, and desirably, the number of iterations per unit time (pulse frequency) is in a range of $1.0\times10^3$ pulses/sec (1.0 kpps) to $3\times10^4$ pulses/sec. More desirably, the number of iterations per unit time (pulse frequency) is in a range of $3.0\times10^3$ pulses/sec to $1\times10^4$ pulses/sec.

The more detailed operation principle of the pulse power supply 12 is described in, Katsuji Iida and Takeshi Sakuma, "Ultrashort Pulse Generating Circuit (IES Circuit) through SI Thyristor", SI Device Symposium Lecture Collection (2002), for example.

As shown in FIGS. 1 to 3, the fluid guide section 18 includes a rectifier net unit 88 for uniformly supplying fluid to the discharge electrode section 16.

Though not shown, the rectifier net unit 88 includes one or more rectifier net, and a holder frame for holding the rectifier net from both sides (upstream side and downstream side). Preferably, the opening ratio of the rectifier net is in a range of 10% to 45%.

Further, in the plasma treatment method according to the embodiment of the present invention, at least a surface of the target object 20 is treated by supplying fluid including nitrogen into the discharge electrode section 16 to generate plasma by the electric discharge in the discharge electrode section 16 and applying the resulting active species and the fluid to the target object 20.

In this case, preferably, the electrical energy per area of the discharge electrode section 16 of the pulse power supply 12 is $1.4\times10^4$ (J/cm$^2$) or more. In this manner, it is possible to achieve 4.5 seconds at the maximum as the apparent life of active species. By adopting the fluid flow rate in a range of 20 mm/s to 500 mm/s, as shown in FIG. 1, the separation distance La from the center of the discharge electrode section 16 to the target object 20 becomes in a range of 3 mm to 1700 mm. The apparent life of the active species herein is not the actual life of active species generated by plasma, but a value (time) obtained by dividing the separation distance La in the case where sterilization is confirmed on the surface of the target object of treatment, by the fluid flow rate. That is, active species generated in plasma may directly arrive at the target object of treatment, or in the presence of active species generated in plasma, other active species generated at locations remote from plasma may arrive at the target object of treatment.

Accordingly, in the embodiment of the present invention, in the case of performing plasma treatment such as sterilization, etc, by applying active species generated in plasma indirectly to the target object (target object 20 of treatment), improvement in the efficiency of the plasma treatment is achieved.

Next, sterilization characteristics in the plasma treatment method will be described with reference to FIGS. 9 to 12.

Figure 9:
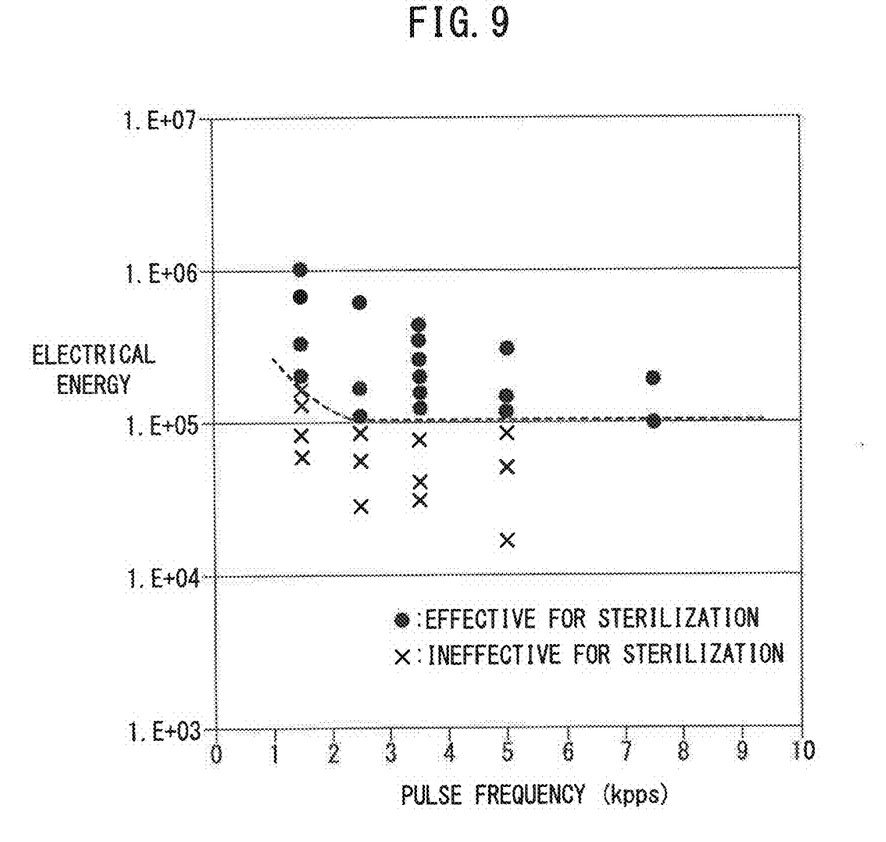
FIG. 9 is a graph showing the relationship between the pulse frequency of high voltage pulse and the electrical energy of the pulse power supply.

FIG. 9 is a graph showing the relationship between the pulse frequency of high voltage pulse and electrical energy of the pulse power supply 12, in the case where the atmosphere around the target object 20 of treatment has 1 atmospheric pressure, the diameter of the through hole of the case is 30 mm, the supply flow rate of a nitrogen gas as fluid is 2 L/min, and the separation distance La is 194 mm. In FIG. 9, points with the sterilization effect are marked by black circle marks, and points without the sterilization effect are marked by X marks. The electrical energy represented by the vertical axis has a logarithmic scale.

As can be seen from FIG. 9, when the pulse frequency is 1.5 kpps, the sterilization effect is obtained at $2.0\times10^5$ (3) or more, and when the pulse frequency is 2.5 kpps, the sterilization effect is obtained at $1.0\times10^5$ (J) or more.

Figure 10:
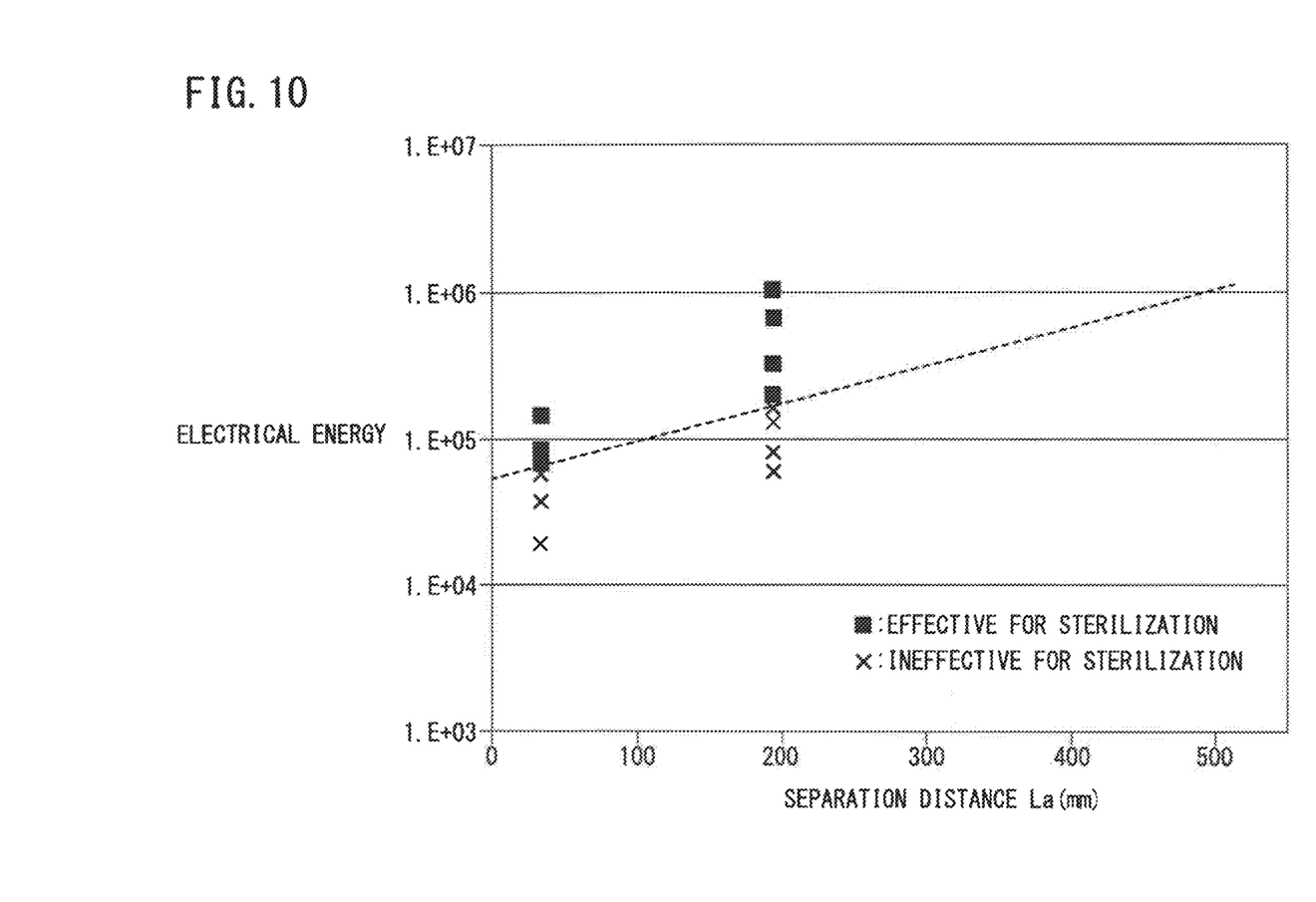
FIG. 10 is a graph showing the relationship between the distance from the center of the discharge electrode section to a target object of treatment and the electrical energy of the pulse power supply.

FIG. 10 is a graph showing the relationship between the separation distance La and the electrical energy of the pulse power supply 12, in the case where the atmosphere around the target object 20 of treatment has 1 atmospheric pressure, the diameter of the through hole of the case is 30 the supply flow rate of the nitrogen gas is 2 L/min, and the pulse frequency is 1.5 kpps. In FIG. 10, points with the sterilization effect are marked by black square marks, and points without the sterilization effect are marked by X marks. The electrical energy represented by the vertical axis has a logarithmic scale.

As can be seen from FIG. 10, when the separation distance La is 34 mm, the sterilization effect is obtained at $6.0\times10^4$ (J) or more, and when the separation distance La is 194 mm, the sterilization effect is obtained at $2.0\times10^5$ (J) or more. The flow rate of the fluid containing nitrogen is 47 mm/s. Therefore, it can be seen from the case where the separation distance La is 194 mm, by conversion, the apparent life of active species is at least 4.12 seconds, as shown in FIG. 11.

Figure 11:
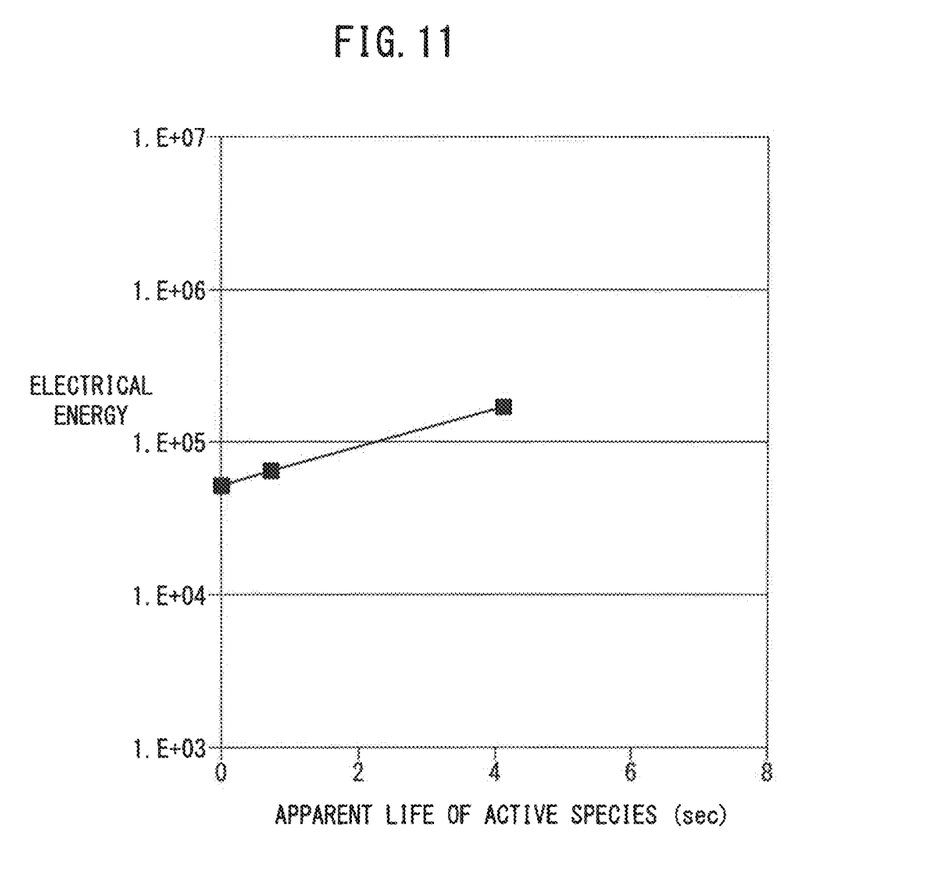
FIG. 11 is a graph showing the relationship between the apparent life of active species generated by plasma and the electrical energy of the pulse power supply.

FIG. 11 is a graph showing the relationship between the apparent life of active species and the electrical energy of the pulse power supply 12, in the case where the atmosphere around the target object 20 of treatment has 1 atmospheric pressure, the diameter of the through hole of the case is 30 the supply flow rate of the nitrogen gas is 2 L/min, and the pulse frequency is 1.5 kpps. The electrical energy represented by the vertical axis has a logarithmic scale.

As shown in FIG. 11, as the increase in the electrical energy of the pulse power supply 12, the apparent life of active species becomes long. If the electrical energy of the pulse supply 12 is $1.0\times15^5$ (J) or more, it is possible to achieve the apparent life of 2 seconds or more which is sufficient in practical applications.

Figure 12:
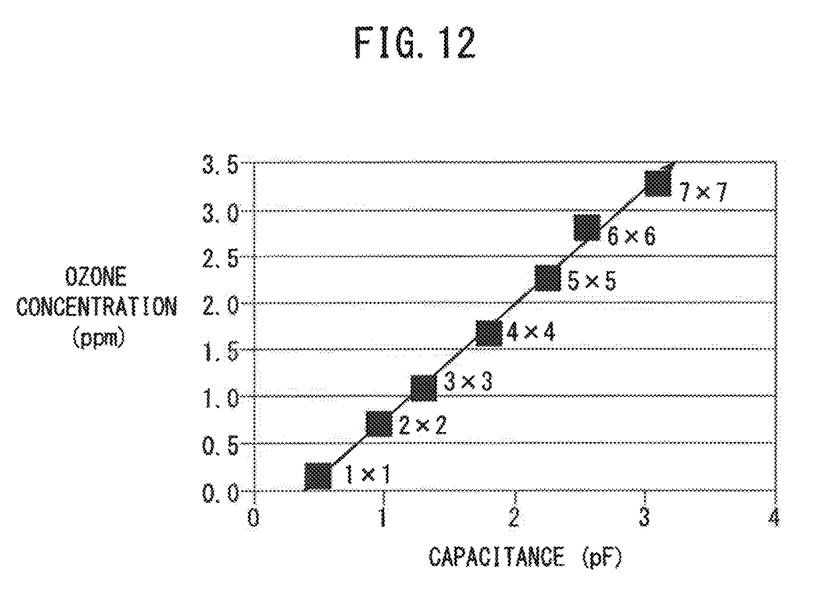
FIG. 12 is a graph showing the relationship between the capacitance between the first discharge electrode of an anode and the second discharge electrode of a cathode, and the concentration of ozone produced in the discharge electrode section.

FIG. 12 is a graph showing the relationship between the capacitance between the first discharge electrode 26A of the anode and the second discharge electrode 26B of the cathode, and concentration of the ozone produced in the discharge electrode section 16. In the graph, the supply flow rate of the air as fluid is 860 L/min, and the pulse frequency is 1.0 kpps. The capacitance between the first discharge electrode 26A and the second discharge electrode 26B is shown by the number of crossing portions between the first electrode section 36A and the second electrode section 36B. In FIG. 12, the number of crossing portions in the case where one first electrode section 36A and one second electrode section 36B are present is denoted by 1×1. In the same manner, the number of crossing portions where two first electrode sections 36A and two second electrode sections 36B are present, three first electrode sections 36A and three second electrode sections 36B are present, . . . seven first electrode sections 36A and seven second electrode sections 36B are present, are denoted by 2×2, 3×3, . . . 7×7, respectively.

As can be seen from FIG. 12, as the increase in the number of crossing portions, i.e., as the increase in the capacitance between the first discharge electrode 26A and the second discharge electrode 26B, concentration of the produced ozone becomes high. As structure of increasing crossing portions, the number of first electrode sections 36A of the first discharge electrode 26A and the number of second electrode sections 36B of the second discharge electrode 26B may be increased. For example, the first discharge electrode 26A may be provided on each of both sides of the second discharge electrode 26B such that the second discharge electrode 26B is interposed between the first discharge electrodes 26A to provide three-stage structure. It is a matter of course that structure of four or more stages may be adopted.

It should be noted that, in the case of fabricating the first discharge electrodes 26A and the second discharge electrodes 26B, preferably, a gel-cast method is used. In the gel-cast method, the first conductor 30A is set in a mold. After slurry including ceramic powder, dispersion medium, and gelling agent are poured into the mold, this slurry is placed in a predetermined temperature condition, or an additive such as crosslinking agent is added to the slurry for gelling the slurry. Thus, the slurry is solidified, and molded. Thereafter, the slurry is fired to fabricate the first discharge electrode 26A. The second discharge electrode 26B can be fabricated in the same manner. In this gel-cast method, since slurry in a low viscosity state is mixed with the first conductor 30A, no pores tend to be formed after mixing. Therefore, in the case where firing is performed after molding to fabricate the first discharge electrode 26A, the dense state of the first ceramic layer 34A is maintained. Further, the dense state of the second ceramic layer 34B can be maintained as well.

It is a matter of course that the plasma treatment method according to the present invention is not limited to the embodiments described above, and various structures can be adopted without deviating the gist of the present invention.

What is claimed is:

1. A plasma treatment method for treating at least a surface of a target object using a plasma treatment apparatus at least including a discharge electrode section having an anode and a cathode and being configured to cause electric discharge between the anode and the cathode based on supply of a high voltage pulse from a pulse power supply, by supplying fluid including nitrogen into the discharge electrode section to generate plasma by the electric discharge in the discharge electrode section and applying resultant active species and the fluid to the target object, wherein a flow rate of the fluid is in a range of 20 mm/s to 500 mm/s;

electrical energy per area of the discharge electrode section in the pulse power supply is $1.4 \times 10^4$ J/cm$^2$ or more; and the target object is positioned outside of the discharge electrode section by a separation distance in a range of 3 mm to 1700 mm from a center of the discharge electrode section.

2. The plasma treatment method according to claim 1, wherein the separation distance is in a range of 30 mm to 500 mm.

3. The plasma treatment method according to claim 1, wherein a pulse frequency of the high voltage pulse outputted from the pulse power supply is in a range of $1 \times 10^3$ pulses/sec to $3 \times 10^4$ pulses/sec.

4. The plasma treatment method according to claim 1, wherein the pulse frequency of the high voltage pulse outputted from the pulse power supply is in a range of $3 \times 10^3$ pulses/sec to $1 \times 10^4$ pulses/sec.

5. The plasma treatment method according to claim 1, wherein the discharge electrode section includes one or more first discharge electrodes as the anode and one or more second discharge electrodes as the cathode; and the first discharge electrode and the second discharge electrode are arranged and separated from each other in a flow direction of the fluid.

6. The plasma treatment method according to claim 5, wherein the first discharge electrode includes one or more first electrode sections having a first conductor;

the second discharge electrode includes one or more second electrode sections having a second conductor; and the first electrode section and the second electrode section are separated from each other, and as viewed from the flow direction of the fluid to the discharge electrode section, the first electrode section and the second electrode section have a crossing positional relationship.

7. The plasma treatment method according to claim 6, wherein as viewed from the flow direction of the fluid to the discharge electrode section, the first electrode section and the second electrode section form a plurality of grids.

8. The plasma treatment method according to claim 6, wherein as viewed from the flow direction of the fluid to the discharge electrode section, number of crossing portions between the first electrode section and the second electrode section is in a range of 1 to 25 portions per square centimeters.

9. The plasma treatment method according to claim 8, wherein the arrangement pitch of the crossing portions is in a range of 2 to 15 mm.

10. The plasma treatment method according to claim 9, wherein the arrangement pitch of the crossing portions is in a range of 4 to 6.5 mm.

11. The plasma treatment method according to claim 6, wherein a ratio of a distance between high potential electrodes to a distance between facing electrodes is in a range of 0.5 to 3.

12. The plasma treatment method according to claim 6, wherein a ratio of a distance between high potential electrodes to a distance between facing electrodes is in a range of 0.8 to 1.3.

13. The plasma treatment method according to claim 6, wherein the first electrode section includes the first conductor and a first ceramic layer covering the first conductor; and the second electrode section includes the second conductor and a second ceramic layer covering the second conductor.

14. The plasma treatment method according to claim 1, wherein the pulse power supply includes a pulse generator configured to apply the high voltage pulse between the anode and the cathode and a pulse controller configured to control the pulse generator to generate electric discharge between the anode and the cathode;

the pulse generator includes a pulse generator circuit having a transformer and a switch connected in series at both ends of a direct current power supply unit, and being configured to accumulate inductive energy in the transformer when ON control of the switch is implemented by the pulse controller, and to generate the high voltage pulse on a secondary side of the transformer when OFF control of the switch is implemented by the pulse controller.

* * * * *